United States Patent [19]
Colotta et al.

[11] Patent Number: 5,739,282
[45] Date of Patent: Apr. 14, 1998

[54] INTERLEUKIN-1 ANTAGONIST

[75] Inventors: Francesco Colotta; Marta Muzio; Alberto Mantovani, all of Milan, Italy

[73] Assignee: Applied Research Systems ARS Holding N.V., Curacao, Netherlands

[21] Appl. No.: 476,860

[22] Filed: Jun. 7, 1995

[30] Foreign Application Priority Data

Oct. 13, 1994 [IT] Italy .................... MI94A2097

[51] Int. Cl.$^6$ .................... C07K 14/47; C12N 15/11
[52] U.S. Cl. .................... 530/350; 435/69.1; 435/70.1; 435/91.2; 435/172.3; 536/23.5
[58] Field of Search .................... 435/69.1, 172.3; 530/350; 935/11, 22, 66; 930/141; 536/23.5

[56] References Cited

U.S. PATENT DOCUMENTS 5,455,330  10/1995  Haskill et al. .................... 530/350

FOREIGN PATENT DOCUMENTS

| A-73636/91 | 3/1991 | Australia . |
| 0 343 684 A1 | 11/1989 | European Pat. Off. . |
| 0 541 920 A1 | 5/1993 | European Pat. Off. . |
| WO 91/08285 | 6/1991 | WIPO . |
| WO 91/17184 | 11/1991 | WIPO . |
| WO 91/17249 | 11/1991 | WIPO . |

OTHER PUBLICATIONS

C. Butcher et al. "Comparison of two promoters controlling expression of secreted or intracellular IL–1 receptor antagonist", Journal of Immunology, vol. 153, Jul. 1994, pp. 701–711.

C. A. Dinarello et al. "Blocking Il–1: Interleukin 1 receptor antagonist in vivo and in vitro", Immunology Today, vol. 12, No. 11, 1991, Cambridge GB, pp. 404–410.

N.F. Zander et al. "cDNA cloning and complete primary structure of skeletal muscle phosphorylase kinase (alpha subunit)", Proceedings of the National Academy of Sciences USA, vol. 85, May 1988, Washington US, pp. 2929–2933. Abstract, EMBL database entry SKADECYC Accession No. X56042 (version 1); 19 Nov. 1990; Young et al.

M. Muzio et al. "Cloning and charcterization of a new isoform of the interleukin 1 receptor antagonist", Journal of Experimental Medicine, vol. 182, No. 2, 1 Aug. 1995, pp. 623–628.

Hannum, Charles H. et al., "Interleukin–1 receptor antagonist activity of a human interleukin–1 inhibitor." Nature, vol. 343, pp. 336–340 (Jan. 25, 1990).

Eisenberg, Stephen P. et al., "Primary structure and functional expression from complementary DNA of a human interleukin–1 receptor antagonist." Nature, vol. 343, pp. 341–346 (Jan. 5, 1990).

Carter, D.B. et al., "Purification, cloning, expression and biological characterization of an interleukin–1 receptor antagonist protein." Nature, vol. 344, pp. 633–638 (Apr. 12, 1990).

Bienkowski, Michael J. et al., "Purification and characterization of interleukin–1 receptor level antagonist proteins from THP–1 cells." Journal of Biological Chemistry, vol. 265, No. 24, pp. 14505–14511 (1990).

Stockman et al. Secondary Strucutre and Topology of Interleukin–1 Receptor Antagonist Protein Determined by Heteronuclear Three–Dimensional NMR Spectorscopy. American Chemical Society vol. 31, No. 23, pp. 5237–5244, Jun. 19, 1992.

Interleukin 1 Receptor Antagonist is a Member of the Interleukin 1 Gene Family: Evolution of a Cytokine Control Mechanism, Proc. Natl. Acad. Sci., vol. 88, pp. 5232–5236, Jun. 1991.

Haskill et al, cDNA Cloning of an Intracelluar Form of the Human Interleukin 1 Receptor Antagonist Associated with Epithelium, Proc. Natl. Acad. Sci., vol. 88 pp. 3681–3685, May 1991.

Primary Examiner—John Ulm
Assistant Examiner—Prema Mertz
Attorney, Agent, or Firm—Browdy and Neimark

[57] ABSTRACT

It is described a new interleukin-1 antagonist active both against IL-1α and IL-1β, a new DNA sequence encoding the Il-1 antagonist and the method for obtaining a IL-1 antagonist by the recombinant DNA technique; it is also described the prophylactic, therapeutic and diagnostic use of such new IL-1 antagonist in pathologies deriving from the IL-1 production.

2 Claims, 3 Drawing Sheets

FIG. 1

Secreted IL-1ra

GAATTCCGGGCTGCAGTCACAGAATGGAAATCGAGAGGCCTCCGCAGTCACCTAATCACTCTCCTCTTCCTGTTCCATTCAG
                        MetGluIleCysArgGlyLeuArgSerHisLeuIleThrLeuLeuLeuPheLeuPheHisSer

Intracellular IL-1ra type I

CAGAAGACCTCCTGTCCTATGAGGCCCTCCCCATGGCTTTAG
                                    MetAlaLeu

← IRA 1

Intracellular IL-1ra Type II

CAGAAGACCTCCTGTCCTATGAGGCCCTCCCCATGGCTTTAGCTGACTTGTATGAAGAAGGAGGTGGAGGAGGAGAAGGTGAAGACAATGCTGACTCAAAGG
                                    MetAlaLeuAlaAspLeuTyrGluGluGlyGlyGlyGlyGlyGluAspAsnAlaAspSerLys ← IRA 1                                                                               IRA 5 →

Common IL-1ra sequence

AGACGATCTGCCACCCTCGACCCTCTGGGAGAAATCAGCAAGATGCAAGCCTTCAGAATCTGGGATGTTAACCAGAGACCTTCTATCTGAGGAACAACCAACTAGTT
GluThrIleCysArgProSerGlyArgArgProAsnAlaPheArgIleTrpAspValAsnGlnArgProSerIleLeuArgAsnAsnGlnLeuVal

GCTGGATACTTGCAAGGACACCAAGCCTGCAAGATGTCAATTTAGAAGAAAAGATAGATGGTGTACCATTGGTAGTGGTATCAAGCCTCATGCTCTGTTCTTCTTGGAATCCATGGAGGGAAGATGTGC
AlaGlyTyrLeuGlnGlyAspThrLysProCysLeuGlnCysMetGluLysGlyIleAspGlyValValProIleGluAspLeuHisAlaLeuPheLeuGlyIleHisGlyGlyLysMetCys

CTGTCCTGTGTCAAGTCTGTGATGAGACCAGATCTGGAGCCAGTTAACATCACTGACCTGAGCGAGAACAGAAAGCAGGACAAGCGCTTCGCCTTCATC
LeuSerCysValLysSerValAspGluThrArgLeuGlnLeuGluAlaValAsnIleThrAspLeuSerGluAsnArgLysGlnAspLysArgPheAlaPheIle

CGCTCAGACAGTGGCCCCACCACCAGTTTGAGTCGCCGCCCCGTTGTTCCTCGCACGATGAAGCTGACCAGCCGTGACCAGCCTCAGCCTCACCAATATG
ArgSerAspSerGlyProThrThrSerPheGluSerAlaAlaCysProGlyTrpPheLeuCysThrAlaMetGluAlaAspGlnProValSerLeuThrAsnMet

CCTGACGAAGGCGTCATGGTCACCAAATTCTACTTCCAGGAGGACGAGTAC
ProAspGluGlyValMetValThrLysPheTyrPheGlnGluAspGlu*

← IRA 4

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: NO     ( i x ) FEATURE:
        ( D ) OTHER INFORMATION: RT-PCR oligonucleotide named IRA5

( x i ) SEQUENCE DESCRIPTION: SEQ ID NO: 1:

CTGACTTGTA TGAAGAAGGA GGTGG                       25

( 2 ) INFORMATION FOR SEQ ID NO: 2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: NO     ( i x ) FEATURE:
        ( D ) OTHER INFORMATION: RT-PCR oligonucleotide corresponding to 60-79 of B-actin     ( x i ) SEQUENCE DESCRIPTION: SEQ ID NO: 2:

GCGCTCGTCG TCGACAACGG                            20

( 2 ) INFORMATION FOR SEQ ID NO: 3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: NO     ( i x ) FEATURE:
        ( D ) OTHER INFORMATION: RT-PCR backward oligonucleotide complementary to 430-449

( x i ) SEQUENCE DESCRIPTION: SEQ ID NO: 3:

GATAGACAAC GTACATGGCT G                        21

( 2 ) INFORMATION FOR SEQ ID NO: 4:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear   ( i i ) MOLECULE TYPE: DNA   ( i i i ) HYPOTHETICAL: NO   ( i x ) FEATURE:
    ( D ) OTHER INFORMATION: Sequence of sIL-1ra not in common   ( i x ) FEATURE:
    ( A ) NAME/KEY: CDS
    ( B ) LOCATION: 24..86

( x i ) SEQUENCE DESCRIPTION: SEQ ID NO: 4:

```
GAATTCCGGG CTGCAGTCAC AGA ATG GAA ATC TGC AGA GGC CTC CGC AGT           50
                         Met Glu Ile Cys Arg Gly Leu Arg Ser
                          1                5

CAC CTA ATC ACT CTC CTC CTC TTC CTG TTC CAT TCA G                       87
His Leu Ile Thr Leu Leu Leu Phe Leu Phe His Ser
 10              15                      20
```

( 2 ) INFORMATION FOR SEQ ID NO: 5:

( i ) SEQUENCE CHARACTERISTICS:
    ( A ) LENGTH: 21 amino acids
    ( B ) TYPE: amino acid
    ( D ) TOPOLOGY: linear   ( i i ) MOLECULE TYPE: protein   ( x i ) SEQUENCE DESCRIPTION: SEQ ID NO: 5:

```
Met Glu Ile Cys Arg Gly Leu Arg Ser His Leu Ile Thr Leu Leu Leu
 1               5                  10                      15

Phe Leu Phe His Ser
             20
```

( 2 ) INFORMATION FOR SEQ ID NO: 6:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear   ( i i ) MOLECULE TYPE: DNA   ( i i i ) HYPOTHETICAL: NO   ( i x ) FEATURE:
    ( D ) OTHER INFORMATION: Sequence of intracellular IL-1ra
      type1 not in common   ( i x ) FEATURE:
    ( A ) NAME/KEY: CDS
    ( B ) LOCATION: 33..41

( x i ) SEQUENCE DESCRIPTION: SEQ ID NO: 6:

```
CAGAAGACCT CCTGTCCTAT GAGGCCCTCC CC ATG GCT TTA G                       42
                                    Met Ala Leu
                                     1
```

( 2 ) INFORMATION FOR SEQ ID NO: 7:

( i ) SEQUENCE CHARACTERISTICS:
    ( A ) LENGTH: 105 base pairs
    ( B ) TYPE: nucleic acid ( C ) STRANDEDNESS: single
( D ) TOPOLOGY: linear ( i i ) MOLECULE TYPE: DNA ( i i i ) HYPOTHETICAL: NO ( i x ) FEATURE:
( D ) OTHER INFORMATION: Sequence of intracellular IL-1ra typeII not in common ( i x ) FEATURE:
( A ) NAME/KEY: CDS
( B ) LOCATION: 33..104

( x i ) SEQUENCE DESCRIPTION: SEQ ID NO: 7:

| CAGAAGACCT | CCTGTCCTAT | GAGGCCCTCC | CC | ATG | GCT | TTA | GCT | GAC | TTG | TAT | 53 |
|---|---|---|---|---|---|---|---|---|---|---|---|
| | | | | Met | Ala | Leu | Ala | Asp | Leu | Tyr | |
| | | | | 1 | | | | 5 | | | |

| GAA | GAA | GGA | GGT | GGA | GGA | GGA | GGA | GAA | GGT | GAA | GAC | AAT | GCT | GAC | TCA | 101 |
|---|---|---|---|---|---|---|---|---|---|---|---|---|---|---|---|---|
| Glu | Glu | Gly | Gly | Gly | Gly | Gly | Gly | Glu | Gly | Glu | Asp | Asn | Ala | Asp | Ser | |
| | | 10 | | | | | 15 | | | | | 20 | | | | |

| AAG | G | 105 |
|---|---|---|
| Lys | | |

( 2 ) INFORMATION FOR SEQ ID NO: 8:

( i ) SEQUENCE CHARACTERISTICS:
( A ) LENGTH: 24 amino acids
( B ) TYPE: amino acid
( D ) TOPOLOGY: linear ( i i ) MOLECULE TYPE: protein ( x i ) SEQUENCE DESCRIPTION: SEQ ID NO: 8:

| Met | Ala | Leu | Ala | Asp | Leu | Tyr | Glu | Glu | Gly | Gly | Gly | Gly | Gly | Gly | Glu |
|---|---|---|---|---|---|---|---|---|---|---|---|---|---|---|---|
| 1 | | | | 5 | | | | | 10 | | | | | 15 | |

| Gly | Glu | Asp | Asn | Ala | Asp | Ser | Lys |
|---|---|---|---|---|---|---|---|
| | | | 20 | | | | |

( 2 ) INFORMATION FOR SEQ ID NO: 9:

( i ) SEQUENCE CHARACTERISTICS:
( A ) LENGTH: 474 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i x ) FEATURE:
( D ) OTHER INFORMATION: Common IL-1ra sequence; a nucleotide G was added in the first position, for computer program reason, in order to encode the first amino acid Glu and further in order to avoid the creation of a stop codon in the inner region of the sequence ( i x ) FEATURE:
( A ) NAME/KEY: CDS
( B ) LOCATION: 1..468

( x i ) SEQUENCE DESCRIPTION: SEQ ID NO: 9:

| GAG | ACG | ATC | TGC | CGA | CCC | TCT | GGG | AGA | AAA | TCC | AGC | AAG | ATG | CAA | GCC | 48 |
|---|---|---|---|---|---|---|---|---|---|---|---|---|---|---|---|---|
| Glu | Thr | Ile | Cys | Arg | Pro | Ser | Gly | Arg | Lys | Ser | Ser | Lys | Met | Gln | Ala | |
| 1 | | | | 5 | | | | | 10 | | | | | 15 | | |

| TTC | AGA | ATC | TGG | GAT | GTT | AAC | CAG | AAG | ACC | TTC | TAT | CTG | AGG | AAC | AAC | 96 |
|---|---|---|---|---|---|---|---|---|---|---|---|---|---|---|---|---|
| Phe | Arg | Ile | Trp | Asp | Val | Asn | Gln | Lys | Thr | Phe | Tyr | Leu | Arg | Asn | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| CAA | CTA | GTT | GCT | GGA | TAC | TTG | CAA | GGA | CCA | AAT | GTC | AAT | TTA | GAA | GAA | 144 |
| Gln | Leu | Val | Ala | Gly | Tyr | Leu | Gln | Gly | Pro | Asn | Val | Asn | Leu | Glu | Glu | |
| | | 35 | | | | | 40 | | | | | 45 | | | | |
| AAG | ATA | GAT | GTG | GTA | CCC | ATT | GAG | CCT | CAT | GCT | CTG | TTC | TTG | GGA | ATC | 192 |
| Lys | Ile | Asp | Val | Val | Pro | Ile | Glu | Pro | His | Ala | Leu | Phe | Leu | Gly | Ile | |
| | | 50 | | | | | 55 | | | | | 60 | | | | |
| CAT | GGA | GGG | AAG | ATG | TGC | CTG | TCC | TGT | GTC | AAG | TCT | GGT | GAT | GAG | ACC | 240 |
| His | Gly | Gly | Lys | Met | Cys | Leu | Ser | Cys | Val | Lys | Ser | Gly | Asp | Glu | Thr | |
| 65 | | | | | 70 | | | | | 75 | | | | | 80 | |
| AGA | CTC | CAG | CTG | GAG | GCA | GTT | AAC | ATC | ACT | GAC | CTG | AGC | GAG | AAC | AGA | 288 |
| Arg | Leu | Gln | Leu | Glu | Ala | Val | Asn | Ile | Thr | Asp | Leu | Ser | Glu | Asn | Arg | |
| | | | | 85 | | | | | 90 | | | | | 95 | | |
| AAG | CAG | GAC | AAG | CGC | TTC | GCC | TTC | ATC | CGC | TCA | GAC | AGT | GGC | CCC | ACC | 336 |
| Lys | Gln | Asp | Lys | Arg | Phe | Ala | Phe | Ile | Arg | Ser | Asp | Ser | Gly | Pro | Thr | |
| | | | 100 | | | | | 105 | | | | | 110 | | | |
| ACC | AGT | TTT | GAG | TCT | GCC | GCC | TGC | CCC | GGT | TGG | TTC | CTC | TGC | ACA | GCG | 384 |
| Thr | Ser | Phe | Glu | Ser | Ala | Ala | Cys | Pro | Gly | Trp | Phe | Leu | Cys | Thr | Ala | |
| | | 115 | | | | | 120 | | | | | 125 | | | | |
| ATG | GAA | GCT | GAC | CAG | CCC | GTC | AGC | CTC | ACC | AAT | ATG | CCT | GAC | GAA | GGC | 432 |
| Met | Glu | Ala | Asp | Gln | Pro | Val | Ser | Leu | Thr | Asn | Met | Pro | Asp | Glu | Gly | |
| | 130 | | | | | 135 | | | | | 140 | | | | | |
| GTC | ATG | GTC | ACC | AAA | TTC | TAC | TTC | CAG | GAG | GAC | GAG | TAGTAC | | | | 474 |
| Val | Met | Val | Thr | Lys | Phe | Tyr | Phe | Gln | Glu | Asp | Glu | | | | | |
| 145 | | | | | 150 | | | | | 155 | | | | | | |

( 2 ) INFORMATION FOR SEQ ID NO: 10:

( i ) SEQUENCE CHARACTERISTICS:
( A ) LENGTH: 156 amino acids
( B ) TYPE: amino acid
( D ) TOPOLOGY: linear ( i i ) MOLECULE TYPE: protein ( x i ) SEQUENCE DESCRIPTION: SEQ ID NO: 10:

| | | | | | | | | | | | | | | |
|---|---|---|---|---|---|---|---|---|---|---|---|---|---|---|
| Glu | Thr | Ile | Cys | Arg | Pro | Ser | Gly | Arg | Lys | Ser | Ser | Lys | Met | Gln | Ala |
| 1 | | | | 5 | | | | | 10 | | | | | 15 | |
| Phe | Arg | Ile | Trp | Asp | Val | Asn | Gln | Lys | Thr | Phe | Tyr | Leu | Arg | Asn | Asn |
| | | | 20 | | | | | 25 | | | | | 30 | | |
| Gln | Leu | Val | Ala | Gly | Tyr | Leu | Gln | Gly | Pro | Asn | Val | Asn | Leu | Glu | Glu |
| | | 35 | | | | | 40 | | | | | 45 | | | |
| Lys | Ile | Asp | Val | Val | Pro | Ile | Glu | Pro | His | Ala | Leu | Phe | Leu | Gly | Ile |
| | | 50 | | | | | 55 | | | | | 60 | | | |
| His | Gly | Gly | Lys | Met | Cys | Leu | Ser | Cys | Val | Lys | Ser | Gly | Asp | Glu | Thr |
| 65 | | | | | 70 | | | | | 75 | | | | | 80 |
| Arg | Leu | Gln | Leu | Glu | Ala | Val | Asn | Ile | Thr | Asp | Leu | Ser | Glu | Asn | Arg |
| | | | | 85 | | | | | 90 | | | | | 95 | |
| Lys | Gln | Asp | Lys | Arg | Phe | Ala | Phe | Ile | Arg | Ser | Asp | Ser | Gly | Pro | Thr |
| | | | 100 | | | | | 105 | | | | | 110 | | |
| Thr | Ser | Phe | Glu | Ser | Ala | Ala | Cys | Pro | Gly | Trp | Phe | Leu | Cys | Thr | Ala |
| | | 115 | | | | | 120 | | | | | 125 | | | |
| Met | Glu | Ala | Asp | Gln | Pro | Val | Ser | Leu | Thr | Asn | Met | Pro | Asp | Glu | Gly |
| | 130 | | | | | 135 | | | | | 140 | | | | |
| Val | Met | Val | Thr | Lys | Phe | Tyr | Phe | Gln | Glu | Asp | Glu | | | | |
| 145 | | | | | 150 | | | | | 155 | | | | | |

( 2 ) INFORMATION FOR SEQ ID NO: 11:

( i ) SEQUENCE CHARACTERISTICS:
( A ) LENGTH: 21 amino acids
( B ) TYPE: amino acid ( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( i x ) FEATURE:
( D ) OTHER INFORMATION: A portion of the intracellular IL-1ra typeII not in common ( x i ) SEQUENCE DESCRIPTION: SEQ ID NO: 11:

```
Ala  Asp  Leu  Tyr  Glu  Glu  Gly  Gly  Gly  Gly  Gly  Gly  Glu  Gly  Glu  Asp
 1              5                        10                        15

Asn  Ala  Asp  Ser  Lys
            20
```

( 2 ) INFORMATION FOR SEQ ID NO: 12:

( i ) SEQUENCE CHARACTERISTICS:
( A ) LENGTH: 579 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i x ) FEATURE:
( D ) OTHER INFORMATION: Intracellular IL-1ra typeII ( i x ) FEATURE:
( A ) NAME/KEY: CDS
( B ) LOCATION: 34..573

( x i ) SEQUENCE DESCRIPTION: SEQ ID NO: 12:

| | | | | |
|---|---|---|---|---|
| CAGAAGGACC TCCTGTCCTA TGAGGCCCTC CCC ATG GCT TTA GCT GAC TTG TAT | | | | 54 |
| | | Met Ala Leu Ala Asp Leu Tyr | | |
| | | 1                   5        | | |

```
GAA  GAA  GGA  GGT  GGA  GGA  GGA  GGA  GAA  GGT  GAA  GAC  AAT  GCT  GAC  TCA      102
Glu  Glu  Gly  Gly  Gly  Gly  Gly  Gly  Glu  Gly  Glu  Asp  Asn  Ala  Asp  Ser
            10                       15                       20

AAG  GAG  ACG  ATC  TGC  CGA  CCC  TCT  GGG  AGA  AAA  TCC  AGC  AAG  ATG  CAA      150
Lys  Glu  Thr  Ile  Cys  Arg  Pro  Ser  Gly  Arg  Lys  Ser  Ser  Lys  Met  Gln
       25                       30                       35

GCC  TTC  AGA  ATC  TGG  GAT  GTT  AAC  CAG  AAG  ACC  TTC  TAT  CTG  AGG  AAC      198
Ala  Phe  Arg  Ile  Trp  Asp  Val  Asn  Gln  Lys  Thr  Phe  Tyr  Leu  Arg  Asn
 40                       45                       50                       55

AAC  CAA  CTA  GTT  GCT  GGA  TAC  TTG  CAA  GGA  CCA  AAT  GTC  AAT  TTA  GAA      246
Asn  Gln  Leu  Val  Ala  Gly  Tyr  Leu  Gln  Gly  Pro  Asn  Val  Asn  Leu  Glu
                 60                       65                       70

GAA  AAG  ATA  GAT  GTG  GTA  CCC  ATT  GAG  CCT  CAT  GCT  CTG  TTC  TTG  GGA      294
Glu  Lys  Ile  Asp  Val  Val  Pro  Ile  Glu  Pro  His  Ala  Leu  Phe  Leu  Gly
                 75                       80                       85

ATC  CAT  GGA  GGG  AAG  ATG  TGC  CTG  TCC  TGT  GTC  AAG  TCT  GGT  GAT  GAG      342
Ile  His  Gly  Gly  Lys  Met  Cys  Leu  Ser  Cys  Val  Lys  Ser  Gly  Asp  Glu
            90                       95                      100

ACC  AGA  CTC  CAG  CTG  GAG  GCA  GTT  AAC  ATC  ACT  GAC  CTG  AGC  GAG  AAC      390
Thr  Arg  Leu  Gln  Leu  Glu  Ala  Val  Asn  Ile  Thr  Asp  Leu  Ser  Glu  Asn
      105                      110                      115

AGA  AAG  CAG  GAC  AAG  CGC  TTC  GCC  TTC  ATC  CGC  TCA  GAC  AGT  GGC  CCC      438
Arg  Lys  Gln  Asp  Lys  Arg  Phe  Ala  Phe  Ile  Arg  Ser  Asp  Ser  Gly  Pro
120                      125                      130                      135

ACC  ACC  AGT  TTT  GAG  TCT  GCC  GCC  TGC  CCC  GGT  TGG  TTC  CTC  TGC  ACA      486
```

| | | | | | | | | | | | | | | |
|---|---|---|---|---|---|---|---|---|---|---|---|---|---|---|
| Thr | Thr | Ser | Phe | Glu 140 | Ser | Ala | Ala | Cys | Pro 145 | Gly | Trp | Phe | Leu | Cys Thr 150 |

```
GCG ATG GAA GCT GAC CAG CCC GTC AGC CTC ACC AAT ATG CCT GAC GAA    534
Ala Met Glu Ala Asp Gln Pro Val Ser Leu Thr Asn Met Pro Asp Glu
            155             160             165

GGC GTC ATG GTC ACC AAA TTC TAC TTC CAG GAG GAC GAG TAGTAC         579
Gly Val Met Val Thr Lys Phe Tyr Phe Gln Glu Asp Glu
        170             175             180
```

(2) INFORMATION FOR SEQ ID NO: 13:

(i) SEQUENCE CHARACTERISTICS:
      (A) LENGTH: 180 amino acids
      (B) TYPE: amino acid
      (D) TOPOLOGY: linear (ii) MOLECULE TYPE: protein (xi) SEQUENCE DESCRIPTION: SEQ ID NO: 13:

```
Met Ala Leu Ala Asp Leu Tyr Glu Glu Gly Gly Gly Gly Gly Glu
 1           5               10                  15

Gly Glu Asp Asn Ala Asp Ser Lys Glu Thr Ile Cys Arg Pro Ser Gly
            20              25              30

Arg Lys Ser Ser Lys Met Gln Ala Phe Arg Ile Trp Asp Val Asn Gln
        35              40              45

Lys Thr Phe Tyr Leu Arg Asn Asn Gln Leu Val Ala Gly Tyr Leu Gln
    50              55              60

Gly Pro Asn Val Asn Leu Glu Glu Lys Ile Asp Val Val Pro Ile Glu
 65              70              75              80

Pro His Ala Leu Phe Leu Gly Ile His Gly Gly Lys Met Cys Leu Ser
                85              90              95

Cys Val Lys Ser Gly Asp Glu Thr Arg Leu Gln Leu Glu Ala Val Asn
            100             105             110

Ile Thr Asp Leu Ser Glu Asn Arg Lys Gln Asp Lys Arg Phe Ala Phe
        115             120             125

Ile Arg Ser Asp Ser Gly Pro Thr Thr Ser Phe Glu Ser Ala Ala Cys
    130             135             140

Pro Gly Trp Phe Leu Cys Thr Ala Met Glu Ala Asp Gln Pro Val Ser
145             150             155             160

Leu Thr Asn Met Pro Asp Glu Gly Val Met Val Thr Lys Phe Tyr Phe
                165             170             175

Gln Glu Asp Glu
        180
```

INTERLEUKIN-1 ANTAGONIST

FIELD OF THE INVENTION

The present invention is in the field of biotechnology, and relates to a novel interleukin-1 (IL-1) antagonist active against both IL-1α and IL-1β, to a new DNA sequence encoding the IL-1 antagonist and to a method for obtaining a IL-1 antagonist by recombinant DNA techniques. The present invention also relates to the prophylactic, therapeutic and diagnostic use of such a novel IL-1 antagonist in pathologies associated with the IL-1 production.

BACKGROUND OF THE INVENTION

Two distinct genes, designated IL-1α and IL-1β, encode for interleukin-1 (IL-1) proteins IL-1α and IL-1β, respectively.

Interleukin IL-1α and IL-1β are pleiotropic cytokines, and each, despite little sequence homology between them, exerts a variety of similar effects on different tissues and act on many human pathologies, and particularly on the immune response of the organism and on inflammatory processes. Both proteins have a molecular weight of about 17.5 kDa and are synthesized as a larger precursor molecule having a molecular weight of about 31 kDa.

IL-1 proteins are potent inflammatory and pyrogenic cytokines that normally have beneficial effects, but that can also have extremely harmful effects on the organism. For example, IL-1 proteins participate in the pathogenesis of autoimmune pathologies, such as lupus erythrmatosus, and in particular, they are involved as mediators that provoke damage to tissues, as for example in rheumatoid arthritis.

Many of the biological effects of IL-1 are similar to those observed during sepsis. Recent studies demonstrated that the intravenous administration of IL-1 in a dosage range from 1 to 10 ng/kg gives rise to fever, sleepiness, anorexy, generalized myalgia, arthralgia and cephalea. Since IL-1 has pleiotropic biological activities, many of which negatively influence the organism, the powerful effects of IL-1 should be put under strict physiological control.

The synthesis of IL-proteins is inhibited by anti-inflammatory cytokines, prostaglandins and glucocorticoids and the existence of multiple levels of inhibition of IL-1 points to the necessity for strict control of this mediator. To date, IL-1 is the only cytokine for which an antagonist polypeptide for the receptor has been described; the third known component of the IL-1 family is the antagonist for the IL-1 receptor (IL-1ra).

All three components (IL-1α, IL-1β, IL-1ra) recognize and bind to the same receptor on the cell surface (IL-1R); the binding of IL-1α and IL-1β to IL-1R transmit a signal, whereas the binding of IL-1ra does not. There are two types of IL-1 receptors designated IL-1RI and IL-1RII. IL-1ra is a polypeptide which binds to IL-1RI, and also binds to IL-1RII with less affinity, without any agonistic activity.

IL-1ra production is induced in different types of cells, including mononuclear phagocytes, polymorphonuclear cells (PMN) and fibroblasts, by IgG, cytokines and bacterial products. Until now, only two molecular forms of IL-1ra have been identified and cloned:

1) secreted IL-1ra (sIL-1ra) contains a classical leader sequence of 25 amino acids giving a mature protein of 152 amino acids;

2) intracellular IL-1ra (icIL-1ra) lacks a leader sequence and it is predicted that this protein remains intracellular. sIL-1ra and icIL-1ra are generated from the same gene.

2

Transcripts of icIL-1ra1 originate from an alternative starting site and from the splicing of a first alternative exon into an internal splice acceptor site located in the first exon of sIL-1ra. The predicted proteins are thus identical except in their NH$_2$ ends, where the first 21 amino acids of sIL-1ra are substituted by four amino acids in icIL-1ra. The expression of transcripts encoding sIL-1ra and icIL-1ra is regulated differently, and the biological significance of icIL-1ra is still unclear.

Considering that IL-1 is involved in pathogenesis of many diseases, it is evident that there is a need for medicaments which are useful in limiting the harmful effects of IL-1.

SUMMARY OF THE INVENTION

An object of the present invention is to provide an IL-1 antagonist active against both IL-1α and IL-1β and against a combination thereof.

Another object of the present invention is to provide a DNA sequence encoding an IL-1 antagonist and a method for obtaining such a novel antagonist by recombinant DNA techniques.

A further object of the present invention is to provide an antagonist in substantially purified form so as to be suitable for use in pharmaceutical compositions active in pathologies that can be treated by inhibiting IL-1.

Further objects and advantages of the invention will be evident in the following description.

SEQ ID NO:1 reports the sequence of an oligonucleotide designated IRA5 for use in RT-PCR.

SEQ ID NO:2 reports the sequence of an oligonucleotide corresponding to nucleotides 69–70 of β-actin cDNA, for use in RT-PCR.

SEQ ID NO:3 reports the sequence of a backward oligonucleotide, complementary to nucleotides 430–449, for use in RT-PCR.

SEQ ID NO:4 reports the DNA sequence encoding sIL-1ra for the portion which is not in common.

SEQ ID NO:5 reports the amino acid sequence of sIL-1ra for the portion which is not in common.

SEQ ID NO:6 reports the DNA sequence encoding three amino acids of icIL-1raI for the portion which is not in common.

SEQ ID NO:7 reports the DNA sequence encoding icIL-1raII for the portion which is not in common.

SEQ ID NO:8 reports the amino acid sequence of icIL-1raII for the portion which is not in common.

SEQ ID NO:9 reports the DNA sequence encoding IL-1ra for the portion which is in common. With regard to questions related to the "Patentin EPO" program for the preparation of the sequences, a G nucleotide was added in the first position

3 of the sequence in order to encode for the first amino acid Glu, and further in order to avoid the formation of a stop codon in the inner side of the sequence.

SEQ ID NO:10 reports the amino acid sequence of IL-1ra for the portion which is in common.

SEQ ID NO:11 reports the sequence of 21 amino acids representing a icIL-1raII fragment not in common with the other IL-1ras.

SEQ ID NO:12 reports the DNA sequence encoding the complete icIL-1raII.

SEQ ID NO:13 reports the amino acid sequence of complete icIL-1raII.

DETAILED DESCRIPTION OF THE INVENTION

The novel IL-1 antagonist was generated by inserting a new 63 base pairs (bp) sequence between the first icIL-1ra specific exon and the internal acceptor site of the first exon of sIL-1ra and in frame with the DNA encoding icIL-1ra.

The present inventors found using RT-PCR that this novel transcript is expressed in activated monocytes and fibroblasts and in polymorphonuclear cells (PMN). Expression in COS cells revealed that this novel antagonist is mostly intracellular and has a molecular weight (MW) of approximately 25 kDa in SDS-PAGE.

The novel recombinant antagonist was demonstrated to have IL-1 inhibitory activity.

The known icIL-1ra will be referred to as icIL-1ra type I (icIL-1raI), and the novel antagonist, described here and the object of the present invention, will be referred to as icIL-1ra type II (icIL-1raII).

In the section that follows, some methods for obtaining the invention will be described, although equivalent material and method can be used. The following examples are therefore purely illustrative and are non-limiting examples of the invention.

Example 1

Cloning and Characterization of icIL-1raII
Materials and Methods
Reagents

The following commercially available reagents were used for the culture and separation of cells: pyrogen-free saline and distilled water for clinical use; RPMI 1640 medium; DMEM medium; M199 medium; L-glutamine; Percoll; Ficoll-Hypaque; aseptically collected fetal calf serum; endothelial cell growth supplement (ECGS) prepared from bovine brain; Heparin. All reagents contained less than 0.125 EU/ml of endotoxin as confirmed by the Limulus amebocyte lysate assay.

Cells

Human circulating PMN and monocytes were separated from the peripheral blood of healthy donors by centrifugation on a discontinous (46% for monocytes and 62% for PMN) gradient of isoosmotic (285 mOsm) Percoll as described in Colotta F., Peri G., Villa SA., Mantovani A., Rapid killing of actinomycin D treated tumor cells by human mononuclear cells. *J. Immunol.* 132:936, 1984. Cells were recovered at the interface, washed twice in saline, and resuspended in medium.

PMN and monocytes recovery was higher than 90% and the purity was higher than 98% as assessed by morphological examination of stained cytocentrifuged cells. The cell culture medium routinely used for PMN and monocytes was RPMI 1640 with 2 mM L-glutamine and 10% FCS.

Human endothelial cells (EC) were obtained from umbilical veins and cultured as described in detail in the literature (Allavena P., Paganin C., Martin-Padura I., Peri G., Gaboli M., Dejana E., Marchisio P. C., Mantovani A., Molecules and structures involved in the adhesion of natural killer cells to vascular endothelium, *J. Exp. Med.*, 173:439, 1991).

Confluent cells at 2nd–5th passage maintained in M199 medium with 10% FCS supplemented with ECGS (50 µg/ml) and Heparin (100 µg/ml were routinely used.

COS cells were cultivated in DMEM medium with 10% FCS and 8387 fibroblast cells in RPMI 1640 medium with 10% FCS.

After the appropriate treatment, the cells were examined for IL-1ra mRNA or IL-1ra protein as described below.

RT-PCR

Total RNA was extracted by the guanidinium isothiocyanate method with minor modifications.

RT-PCR was performed as described in Colotta F., Polentarutti, N., Sironi M., Mantovani A., *J.Biol.Chem.*, 267:18278, 1992.

Briefly, 1 µg RNA was reverse transcribed in reverse transcriptase buffer (5 mM $MgCl_2$, 50 mM KCl, 10 mM Tris-HCl; pH 8.3) with 2.5 mM random hexamers, 1 mM each deoxynucleotide triphosphate, 1 unit/ml RNase inhibitor, and 2.5 units/ml moloney murine leukemia virus transcriptase (Perkin Elmer Cetus, Norwalk, Conn.). Samples were incubated for 10 min at 25° C. and then at 42° C. for 45 min. Then, a specific pair of primers, designed to amplify cDNAs encoding icIL-1raI or icIL1raII, were added to the cDNA reaction, and, as an internal control, human β-actin was added.

Amplification was carried out in 2 mM $MgCl_2$, 50 mM KCl, 0.2M of each deoxynucleotide triphosphate, 2.5 units/ 100 ml Taq polymerase (Perkin Elmer Cetus) and 4 mg/ml of each specific primer (see below). Amplification (30 cycles) was carried out in an automated thermal cycler (Perkin Elmer Cetus) at 95° C., at 55° C., and at 72° C. for 1.5 min each. Amplified products were run through a 1% ethidium bromide-stained agarose gel along with molecular weight standards (Boehringer Mannheim, Mannheim, Germany).

Oligonucleotides were synthesized by the phosphoramidite method. The sequences of oligonucleotides used to selectively amplify icIL-1ra were identical to those described in Haskill S. et al., *Proc. Natl. Acad. Sci., USA*, 88:3681, 1991. In particular, oligonucleotides GM397 (indicated here as IRA 1) and GM368 (IRA 4) was used. For the icIL-1raII amplification, IRA 4 and IRA 5 (SEQ ID NO:1), which specifically recognizes the extra exon described here to be included in the icIL-1raII sequence, were used.

For β-actin amplification the forward oligonucleotide is presented in SEQ ID NO:2, corresponding to nucleotides 60–79 of β-cDNA. The backward oligonucleotide presented in SEQ ID NO:3, is complementary to nucleotides 430–449. The amplification products were subcloned (TA Cloning System, Invitrogen, San Diego, Calif.) and sequenced by the dideoxy chain termination method.

Expression of icIL-1ra Products in COS Cells

The cDNAs containing 32 bp of the 5'-untranslated region, the complete open reading frame and 6 bp (including the stop codon) of the 3'-untranslated region of both the icIL-1raI and icIL-1raII were obtained by RT-PCR with oligonucleotides IRA 4 and IRA 5 as described above and then ligated back into the pSF5 expression vector. Fidelity of reverse transcription and amplification was verified by sequencing.

The plasmids containing the cDNA in the correct orientation were purified on CsCl gradient and then transfected into COS cells by the calcium precipitate method as described in Sambrook J. et al., Cold Spring Harbor Laboratory Press, 1989.

After two days, culture supernatants and sonicated cell lysates were examined by ELISA or immunoblotting as described below. An empty plasmid (not transfected) was used as a control.

Identification of Immunoreactive IL-1ra

A commercial ELISA test (Amersham, Buckinamshire, UK) that identifies both sIL-1ra and icIL-1ra was used. For the Western blot analysis, polyclonal antisera of two rabbits and of one goat were used. COS cell lysate samples and supernatants were run on 12.5% SDS-PAGE electrophoresis and then blotted onto a nitrocellulose filter (Stratagene, La Jolla, Calif., U.S.A.). Incubation with primary and secondary antibodies was carried out according to standard protocols. The primary antibody was an anti-IL-1ra rabbit polyclonal antibody. The secondary antibody was a goat anti-rabbit immunoglobulin fraction linked to horseradish peroxidase (Amersham). Immunoreactive protein fraction bands were revealed by a chemiluminescence-based procedure (ECL Detection, Amersham) according to manufacturer's instructions.

Il-1-induced Expression of E-selectin on EC

Confluent EC cultivated in 96 well plates (Falcon) were incubated for 30 minutes with an amount of transfected COS cell lysate (see above) corresponding to 25 to 100 ng of recombinant IL-1ra (either icIL-1raI or icIL-1raII) as assessed by a specific ELISA assay (Amersham).

As a control, an equal amount of COS lysate obtained from mock transfected cells was used in parallel. Next, EC were exposed for 6 hours to 0.1–1 ng/ml human recombinant IL-1β. The detection of E-selectin expression was made with an ELISA assay on adherent EC with the anti-E-selectin monoclonal antibody BB1G-E2 as primary antibody and a rabbit anti-mouse Ig antiserum conjugated with horseradish peroxidase as a secondary antibody. Optical Density (O.D.) of the samples was determined by measuring the plates with a spectrophotometer (Flow) at 405 nm wavelength.

Results

Identification of icIL-1raII

Specific oligonucleotide primers were designed (indicated as IRA 1 and IRA 4 in FIG. 1) in order to obtain the entire coding sequence of icIL-1ra (FIG. 1) by RT-PCR. Amplified products from human PMN were subcloned and sequenced.

In addition to the previously known sequence of icIL-1ra, the present inventors isolated a number of clones whose sequences were identical to the published icIL-1ra coding sequence, with the notable exception of an extra sequence of 63 bp between nucleotides 132 and 133 of the icIL-1ra sequence. Given the described exon-intron boundaries of icIL-1ra, the extra sequence is inserted between the first leader-less exon of icIL-1ra and the internal acceptor site of the first exon of sIL-1ra (FIG. 1).

Figure 1:
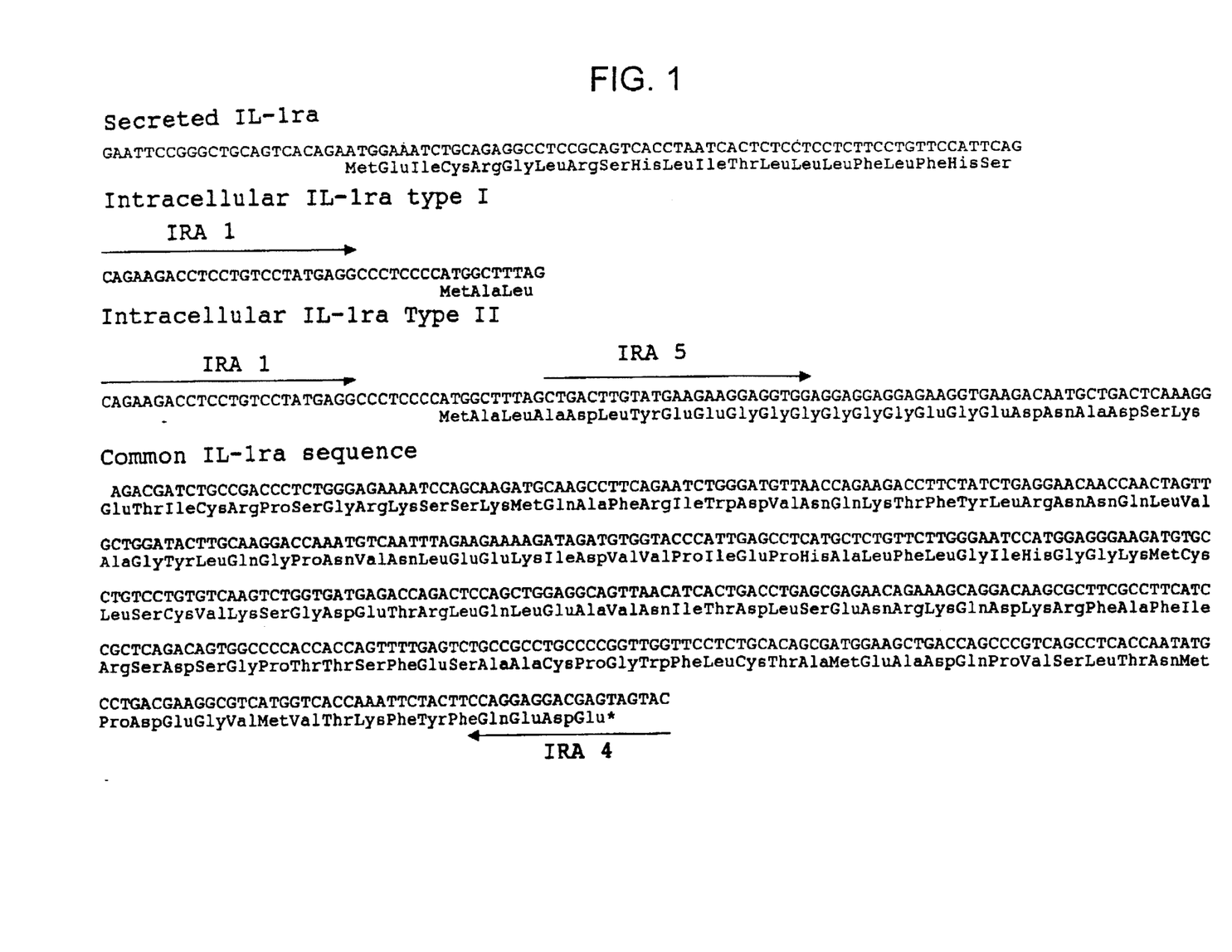
FIG. 1 shows the DNA sequence and the amino acid sequence, for the portion which is not in common, of the icIL-1raII protein (SEQ ID ID NO:7 and SEQ ID NO:8) compared to those of classic sIL-1ra (icIL-1raI; SEQ ID NO:6) and of sIL-1ra (SEQ ID NO:4 and SEQ ID NO:5), and it further shows the DNA sequence and the encoded protein sequence for the portion of IL-1ra in common (SEQ ID NO:12 and SEQ ID NO:13).

The predicted amino acid sequence is shown in FIG. 1. The novel protein (herein referred to as icIL-1ra type II) has the first three amino acids at the NH$_2$ terminus in common with the classical icIL-1ra (icIL-1ra type I), followed by a new sequence of 21 amino acids. The rest of the two proteins is identical.

Surprisingly, the junction with the internal acceptor site of the first exon of sIL-1ra, both for sIL-1ra and icIL-1raI and for icIL-1raII, always generated the same amino acid residue, i.e. glutamic acid (FIG. 1).

The most striking characteristic of the extra inserted amino acid sequence is the presence of seven glycine residues, six of which are consecutive. Glycine residues are flanked on both sides by glutamic acid residues. icIL-1raII consists of 180 amino acids, and the overall hydrophilic pattern of icIL-1raII is similar to that of icIL-1raI, and still lacks an hydrophobic leader peptide at the NH$_2$ terminus.

Expression of icIL-raII

Figure 2A:
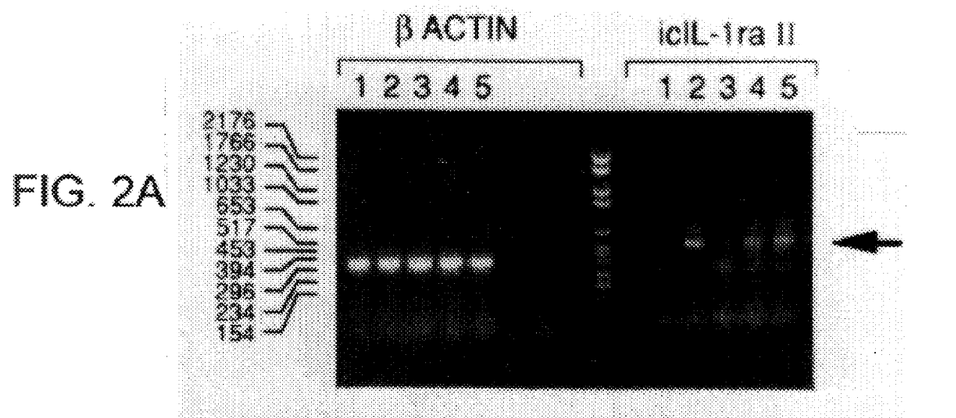
FIGS. 2A, 2B and 2C show the RT-PCR analysis of icIL-1raII expression in different cell types.

To identify icIL-1raII transcripts, RT-PCR analysis was performed with a pair of specifically designed oligonucleotides (IRA 5 and IRA 4, FIG. 1), with an expected amplified product of 533 bp. As shown in FIG. 2A, transcripts encoding icIL-1raII were detectable in PMA-, IL-1- and TNF-activated fibroblasts. A faint but detectable band was evident in LPS-treated monocytes. PMN, either untreated or activated (FIG. 2C), also showed a very faint band of the expected size. The specificity of amplified products indicated in FIGS. 2A, 2B, 2C was confirmed by subcloning and sequencing.

Expression of Recombinant icIL-1raII

COS cells were transfected with the DNA sequence encoding icIL-1raII and, by way of comparison, with that encoding icIL-1raI. Next, cell lysates and supernatants were examined by Western blot.

Figure 3:
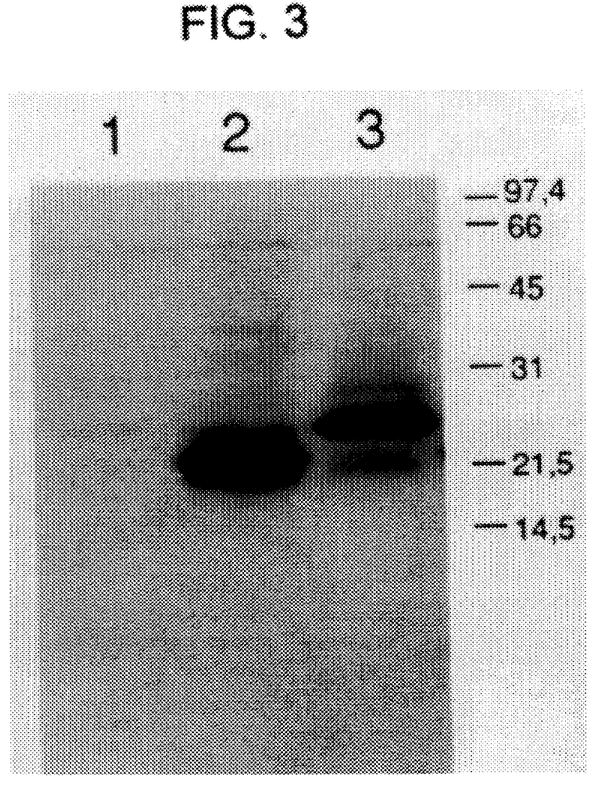
FIG. 3 shows the Western blot analysis of recombinant icIL-1raII.

The polyclonal antisera used in these experiments recognized icIL-1raII and icIL-1raI equally well (FIG. 3). Most, if not all, of icIL-1raII and icIL-1raI were found in cell lysates. Recombinant icIL-1raI migrated as a predominant band of 22 kDa, whereas icIL-1raII showed a mass of approximately 25 kDa.

Inhibition of IL-1B Activity by Recombinant icIL-1raII

Recombinant icIL-1raII was examined for IL-1 inhibiting activity using IL-1-induced expression of E-selectin on endothelial cells. This assay is sensitive (detectable induction at 100 pg/ml IL-1, or less) and rapid (6 hours incubation with IL-1).

Lysates of mock transfected COS cells did not significantly reduce IL-1 activity. icIL-1raII had no antagonistic activity. Recombinant icIL-1raII inhibited in a dose-dependent fashion IL-1 activity. These data provide evidence that icIL-1raII is indeed an inhibitor of IL-1.

Discussion

The present inventors describe a novel molecular form of icIL-1ra which is generated by insertion of 63 bp between the first leader-less exon of icIL-1ra and the internal acceptor site of the first exon of sIL-1ra. Since the resulting protein is partially identical to classical icIL-1ra, with the exception of an extra sequence of 21 amino acids located in the NH$_2$ terminus of the molecule, the present inventors suggest that this novel form be designated as IL-1ra type II, and referring to the classical icIL-1ra sequence as icIL-1ra type I.

RT-PCR experiments demonstrated that icIL-1raII transcripts are inducible in monocytes and fibroblasts. Recombinant icIL-1raII expressed in COS cells had an apparent MW of approximately 25 kDa and an IL-1 inhibitory activity comparable to that exerted by icIL-1raI expressed under the same experimental conditions. Transcripts coding for icIL-1ra and sIL-1ra were generated from the same gene by means of differential splicing. icIL-1ra was generated from an alternative start of transcription of an exon inserted into an internal acceptor site of the first exon containing the leader sequence of sIL-1ra.

The results obtained by the present inventors suggest a new organization for the IL-1ra gene, in which an extra exon is located between the first exon of, respectively, classical icIL-1ra and sIL-1ra. The presence of this extra exon generates a polypeptide molecule which lacks a signal peptide, but differs from icIL-1raI at its N-terminus by the insertion of 21 amino acids, and still remains inhibitory against IL-1.

The use of alternative splicing to generate different IL-1ra molecules appears to be highly regulated. icIL-1raII transcripts were induced by IL-1, TNF and phorbol esters in fibroblasts and by LPS in monocytes. In fibroblasts, phorbol esters were found to selectively induce icIL-1ra transcripts, whereas IL-1 and TNF induced both sIL-1ra and icIL-1ra mRNAs. In monocytes, IL-13, which augmented both transcripts of sIL-1ra and icIL-1raI, failed to induce icIL-1raII.

Finally, PMN, in which sIL-1ra and icIL-1ra are constitutively expressed and inducible, expressed very few transcripts, as demonstrated by RT-PCR. Overall, these results indicate that the mechanisms that induce the differential splicing, which generate the three forms of IL-1ra, are differentially regulated in response to external signals.

The amino acid sequence of the extra sequence described here is surprising in that it contains seven residues of glycine, six of which are consecutive. Glycine-rich sequences are present in molecules with different biological activities, including the atrial natriuretic clearance receptor, the HOX11 homeobox gene, the intermediate filaments keratins and nuclear proteins involved in centromere binding or RNA splicing.

Apart from glycine residues, however, no obvious homology was evident between these proteins and icIL-1raII in the amino acid sequence flanking the glycine-rich regions.

The IL-1 system shows an extraordinary level of complexity, and consists of two agonists, two receptors, one of which is an inhibitor of IL-1, and a receptor antagonist, for which at least three different molecular forms exist, as shown by the results obtained.

Although the biological significance of the intracellular forms of IL-1ra remains to be clearly established, the results reported here indicate that two different forms of icIL-1ra with different N-termini can be generated by alternative splicing in response to selected external stimuli.

The existence of multiple and complex levels of control of IL-1 points to the absolute requirement for a tight physiological control of the inflammatory potential of this cytokine.

DESCRIPTION OF THE FIGURES

FIG. 1

DNA Sequence and Predicted Protein Sequence of icIL-1raII Compared to Classical icIL-1ra(icIL-1raI) and sIL-1ra The upper part of FIG. 1 shows DNA and protein sequences specifically represented in sIL-1ra, icIL-1raI and icIL-1raII. The lower part of FIG. 1 shows the sequence in common among the three forms of IL-1ra. The entire sequence for each molecule is thus generated by the junction of each specific portion with the common sequence. For clarity, the DNA sequence of icIL-1ra starts from nucleotide 91 of the published 5' untranslated sequence, and only 6 bp of the 3' untranslated sequence are reported. The common IL-1ra sequence starts with the internal acceptor site located in the first exon of sIL-1ra, corresponding to nucleotide 133 of the complete icIL-1raI sequence and to nucleotide 88 of the complete sIL-1ra sequence. Arrows indicate forward (IRA 1 and IRA 5) and backward (IRA 4) oligonucleotides used for RT-PCR analysis, as described in the text. The oligonucleotide IRA 5 recognizes only icIL-1raII DNA. The asterisk indicates the stop codon.

Figure 2B:
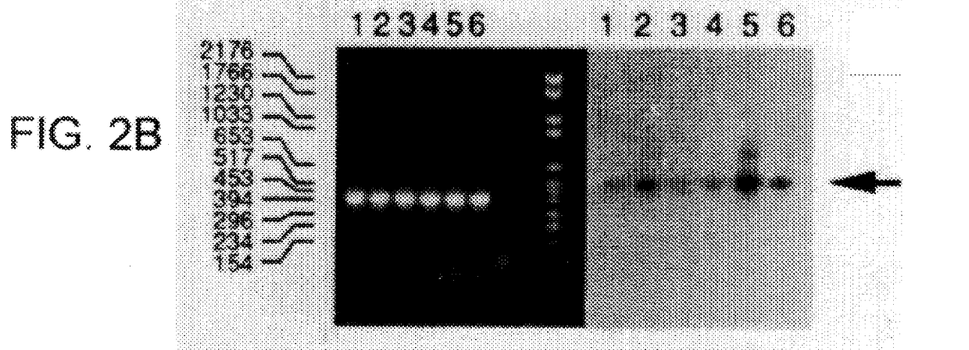
Figure 2C:
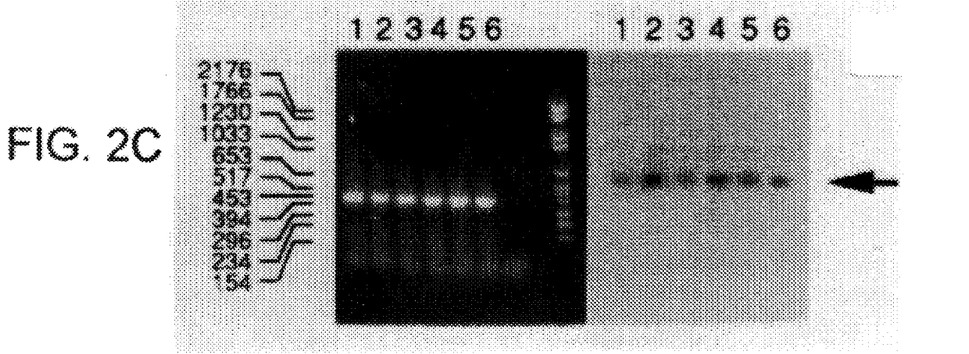

FIGS. 2A, 2B, 2C

RT-PCR Analysis of icIL-1raII Expression in Different Cell Types

RNAs from 8387 fibroblasts (panel FIG. 2A), monocytes (FIG. 2B) and PMN (FIG. 2C) were reverse-transcribed. Each DNA synthesis reaction was then divided into two samples, one of which was amplified with oligonucleotides IRA 5 (forward) and IRA 4 (backward) for detection of icIL-1raII transcripts, and the other sample was amplified with β-actin specific oligonucleotides (see Material and Methods section). Amplified products were then examined through an ethidium bromide-stained agarose gel. Amplified products corresponding to β-actin are reported on the left side of the standard and the amplified products corresponding to icIL-1raII (on the right) are indicated by an arrow. The specificity of these bands was confirmed by subcloning and sequencing.

FIG. 3

Western Blot Analysis of Recombinant icIL-1raII

Cell lysates from COS cells transfected with DNAs encoding icIL-1raI (2) or icIL-1raII (3) or with an empty vector which does not contain such DNA (1) were examined by immunoblotting with an anti-IL-1ra rabbit polyclonal antibody. Molecular weight standards are indicated.

Effects of icIL-1raII on IL-1-induced Expression of E-selectin on Endothelial Cells Endothelial cells were treated with 0.1 or 1 ng/ml of human IL-1β, with or without 25–100 ng/ml of icIL-1raII or equivalent amounts of COS cell lysates obtained from cells which were mock transfected by means of an empty vector, as described in the Material and Method section. After 6 hours of incubation, the endothelial cells were examined for E-selectin expression by an ELISA test performed on adherent cells. The data reported are percentages of IL-1-induced E-selectin expression for the control.

Examples of pathologies in which the novel antagonist according to the present invention can be advantageously used for prophylactic, therapeutic or diagnostic purposes are rheumatoid arthritis, septic shock, acute myelomonocytic leukemia, immunological reaction of transplant against host, acquired immunodeficiency syndrome (AIDS), ulcerative colitis and all autoimmune diseases in general.

An embodiment of the invention is the administration of a pharmacologically active amount of icIL-1raII to people having a high risk of developing pathologies that can be treated by inhibiting IL-1 or to people already showing pathologies like sepsis. An example of the category cited above are patients waiting for a surgical operation.

Any route of administration compatible with the active principle can be used, but parenteral administration is particularly preferred because it permits systemic effects in a short period of time. For this reason, it is preferable that the administration of an intravenous bolus is given just before, during or after the surgical operation. The dose of icIL-1raII to be administered depends on the age, weight and the individual response of the patient. The dosage can be between 0.05 and 30 mg/Kg body weight and the preferable dose is between 0.1 and 10 mg/Kg body weight.

The pharmaceutical composition for parenteral use can be prepared in injectable form and comprises an active principle and a suitable vehicle. Vehicles for the parenteral administration are well known in the art and comprise, for example, water, saline solution, Ringer's solution and dextrose. The vehicle can contain smaller amounts of excipients in order to maintain stability in solution and isotonicity.

The preparation of the above-cited solutions can be carried out according to the ordinary modalities and preferably the icIL-1raII content will be between 1 mg/ml and 10 mg/ml.

Further examples of pathologies wherein the novel antagonist according to the invention can be advantageously used for prophylactic, therapeutic, or diagnostic purposes are rheumatoid arthritis, septic shock, acute myelomonocytic leukemia, immunological reaction of transplants against host, acquired immunodeficiency syndrome (AIDS), ulcerative colitis and all autoimmune diseases in general.

The present invention has been described with reference to the specific embodiments, but the content of the description encompasses all modifications and substitutions which can be brought by a person skilled in the art without extending beyond the meaning and purpose of the following claims.

We claim:

1. A purified protein having antagonist activity against at least one of the substances selected from the group consisting of interleukin-1α and interleukin-1β, and having the amino acid sequence of SEQ ID NO:13.

2. A purified protein according to claim 1, obtained by a recombinant DNA technique.

* * * * *